(12) United States Patent
Meridew et al.

(10) Patent No.: US 9,955,982 B2
(45) Date of Patent: May 1, 2018

(54) FEMORAL DRILL GUIDE CONFIGURED FOR OUTSIDE-IN DRILLING AND INSIDE-OUT REAMING

(71) Applicant: Biomet C.V., Gibraltar (GB)

(72) Inventors: Jason Meridew, Warsaw, IN (US); Daniel Romano, Warsaw, IN (US); Gregory Loren, Encinitas, CA (US)

(73) Assignee: Biomet C.V., Warsaw, IN (US)

( * ) Notice: Subject to any disclaimer, the term of this patent is extended or adjusted under 35 U.S.C. 154(b) by 435 days.

(21) Appl. No.: 14/691,026

(22) Filed: Apr. 20, 2015

(65) Prior Publication Data
US 2016/0302805 A1 Oct. 20, 2016

(51) Int. Cl.
*A61B 17/17* (2006.01)
(52) U.S. Cl.
CPC .............................. *A61B 17/1714* (2013.01)
(58) Field of Classification Search
CPC ...................................... A61B 17/17–17/1792
See application file for complete search history.

(56) References Cited

U.S. PATENT DOCUMENTS

| | | | |
|---|---|---|---|
| 6,120,511 A * | 9/2000 | Chan ................. | A61B 17/1637 606/102 |
| 7,736,364 B2 | 6/2010 | Stone | |
| 7,985,226 B2 * | 7/2011 | McAllister ........... | A61B 17/155 606/88 |
| 8,002,778 B1 | 8/2011 | Meridew | |
| 8,128,658 B2 | 3/2012 | Kaiser et al. | |
| 8,361,113 B2 | 1/2013 | Stone et al. | |
| 8,491,599 B2 * | 7/2013 | Heilala ................. | A61B 17/17 606/99 |
| 8,740,939 B2 | 6/2014 | Stone et al. | |
| 8,986,314 B1 * | 3/2015 | Jordan ............... | A61B 17/1714 606/96 |

(Continued)

OTHER PUBLICATIONS

Conrad, J., MD., "ToggleLoc Inline Device with ZipLoop Technology and TunneLoc Tibial Fixation for ACL Reconstruction—Surgical Technique". Biomet Sports Medicine.

(Continued)

*Primary Examiner* — Zade Coley
(74) *Attorney, Agent, or Firm* — Schwegman Lundberg & Woessner, P.A.

(57) ABSTRACT

A femoral drill guide assembly constructed in accordance to one example of the present disclosure includes a handle portion, a parallel slider, a perpendicular slider, a feeder guide and a receiving guide. The handle portion can extend along a first plane and include a first adjustable mating portion formed thereon. The parallel slider can have a second and a third adjustable mating portion thereon. The first and second adjustable mating portions can selectively move relative to each other causing the parallel slider to move relative to the handle portion between a plurality of positions along the first plane. The perpendicular slider can extend along a second plane and have a fourth adjustable mating portion thereon. The third and fourth adjustable mating portions can selectively move relative to each other causing the perpendicular slider to move relative to the parallel slider between a plurality of positions along the second plane.

22 Claims, 6 Drawing Sheets

(56) References Cited

U.S. PATENT DOCUMENTS

| | | | |
|---|---|---|---|
| 8,986,316 B1* | 3/2015 | Jordan | A61B 17/1714 606/96 |
| 2009/0149858 A1 | 6/2009 | Fanelli et al. | |
| 2010/0160925 A1* | 6/2010 | Heilala | A61B 17/17 606/96 |
| 2012/0059382 A1* | 3/2012 | Paulos | A61B 17/1714 606/96 |
| 2013/0282016 A1* | 10/2013 | Volpi | A61B 17/1714 606/98 |
| 2013/0289573 A1* | 10/2013 | Heilala | A61B 17/17 606/96 |
| 2015/0150570 A1* | 6/2015 | Okuno | A61B 17/1764 606/87 |

OTHER PUBLICATIONS

Gittins, M., DO., "ToggleLoc Fixation Device Femoral Fixation for ACL Reconstruction—Surgical Technique". Biomet Sports Medicine.

* cited by examiner

FEMORAL DRILL GUIDE CONFIGURED FOR OUTSIDE-IN DRILLING AND INSIDE-OUT REAMING

FIELD

The present disclosure relates generally to a method and apparatus for use in performing ACL reconstruction, and more particularly to a method and apparatus including a drill guide assembly that is adjustable in two distinct planes.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

An anterior cruciate ligament (ACL) interconnects a portion of the tibia with a portion of the femur. Although the natural and healthy anatomy generally is able to support the various portions of the anatomy with natural ligaments and tendons such as the ACL, injury, disease, age or other circumstances may cause weakening or breaking of the ACL requiring surgical intervention. The breaking or weakening of the tissue may require the tissue to be reconnected or replaced with various autografts or xenografts that may be made of natural or synthetic materials. These various materials are generally interconnected with selected portions of the anatomy using screws or other similar friction or obstruction holding devices. Typically a surgeon prepares a tunnel in the femur for receipt of the replacement ligament. Correct location of such a femoral tunnel is critical to surgical success. While many instruments available are satisfactory for their intended purpose, it would be desirable to provide a femoral drill guide that offers greater adjustability such that a surgeon can first identify the optimal position of the femoral tunnel and subsequently use the femoral drill guide to assist in preparing that femoral tunnel in a minimally invasive manner.

SUMMARY

This section provides a general summary of the disclosure, and is not a comprehensive disclosure of its full scope or all of its features.

A femoral drill guide assembly constructed in accordance to one example of the present disclosure includes a handle portion, a parallel slider, a perpendicular slider, a feeder guide and a receiving guide. The handle portion can extend along a first plane between a first handle end and an opposite second handle end. The first handle end can include a first adjustable mating portion formed thereon. The parallel slider can extend between a parallel slider first end and an opposite parallel slider second end. The parallel slider can have a second and a third adjustable mating portion thereon. The first and second adjustable mating portions can selectively move relative to each other causing the parallel slider to move relative to the handle portion between a plurality of positions along the first plane. The perpendicular slider can extend along a second plane between a perpendicular slider first end and an opposite perpendicular slider second end. The perpendicular slider can have a fourth adjustable mating portion thereon. The third and fourth adjustable mating portions can selectively move relative to each other causing the perpendicular slider to move relative to the parallel slider between a plurality of positions along the second plane. The feeder guide can be movably coupled to the perpendicular slider and be configured to direct a guide wire. The receiving guide can be coupled to the handle portion and have a receiving end configured to accept the guide wire from the feeder guide.

According to additional features, the receiving end of the receiving guide is funnel-shaped. The receiving guide can comprise a first guide body portion that extends along a first axis and a second guide body portion that extends along a second axis. The first and second guide body portions can converge at an intermediate non-linear body portion. The first and second axes intersect. The receiving guide can be cannulated.

According to other features, one of the first and second adjustable mating portions comprises a first slot. The other of the first and second adjustable mating portions comprises a first locating member. The first locating member can slidably negotiate along the first slot causing the parallel slider to move relative to the handle portion between the plurality of positions along the first plane. The locating member can collectively comprise a first screw that threadably mates with the receiving disk. The first screw is movable between (i) a locked position with the disk wherein the first locating member is fixed to the handle portion and (ii) an unlocked position with the disk wherein the first locating member moves along the first slot and the parallel slider moves relative to the handle portion. The first slot is arcuately shaped along the handle portion.

In other features, one of the third and fourth adjustable mating portions comprises a second slot and the other of the third and fourth adjustable mating portions comprises a second locating member. The second locating member slidably negotiates along the second slot causing the perpendicular slider to move relative to the parallel slider between the plurality of positions along the second plane. The second locating member can collectively comprise a second screw that threadably mates with a receiving member. The second screw can be movable between (i) a locked position with the receiving member wherein the second locating member is fixed to the perpendicular slider and (ii) an unlocked position with the receiving member wherein the second locating member moves along the second slot and the perpendicular slider moves relative to the parallel slider. The second slot is arcuately shaped along the perpendicular slider. The receiving guide is rotatably fixed to the second handle end whereby the receiving guide selectively rotates along the second axis. The second guide body portion of the receiving guide can adjustably translate along the second axis relative to the handle portion to locate the receiving end at a plurality of positions. The parallel slider can be arcuately shaped. The perpendicular slider can be arcuately shaped.

A femoral drill guide assembly constructed in accordance to another example of the present disclosure can include a handle portion, a first adjustable member, a second adjustable member, a feeder guide and a receiving guide. The handle portion can extend along a first plane and include a first adjustable mating portion formed thereon. The first adjustable member can have a second and a third adjustable mating portion formed thereon. The first and second adjustable mating portions selectively move relative to each other causing the first adjustable member to move relative to the handle portion between a plurality of positions along the first plane. The second adjustable member can extend along a second plane and have a fourth adjustable mating portion thereon. The third and fourth adjustable mating portions can selectively move relative to each other causing the second adjustable member to move relative to the first adjustable member between a plurality of positions along the second plane. The first and second planes are distinct. The feeder guide can be movably coupled to the second adjustable member and be configured to direct a guide wire. The receiving guide can be coupled to the handle portion and have a funnel-shaped receiving end configured to accept the guide wire from the feeder guide.

According to other features, the receiving guide can include a first guide body portion that extends along a first axis and a second guide body portion that extends along a second axis. The first and second guide body portions can converge at an intermediate non-linear body portion. The first and second axes intersect. One of the first and second adjustable mating portions comprises a first slot. The other of the first and second adjustable mating portions comprises a first locating member. The first locating member can slidably negotiate along the first slot causing the first adjustable member to move relative to the handle portion between the plurality of positions along the first plane. The first locating member can collectively comprise a first screw that threadably mates with a receiving disk. The first screw is movable between (i) a locked position with the disk wherein the first locating member is fixed to the handle portion and (ii) an unlocked position with the disk wherein the first locating member moves along the first slot and the first adjustable mating portion moves relative to the handle portion.

According to other features, one of the third and fourth adjustable mating portions includes a second slot. The other of the third and fourth adjustable mating portions includes a second locating member. The second locating member slidably negotiates along the second slot causing the second adjustable member to move relative to the first adjustable member between the plurality of positions along the second plane. The second locating member can collectively comprise a second screw that threadably mates with a receiving member. The second screw is movable between (i) a locked position with the receiving member wherein the second locating member is fixed to the second adjustable member and (ii) an unlocked position with the receiving member wherein the second locating member moves along the second slot and the second adjustable member moves relative to the first adjustable member. The first slot is arcuately shaped along the first adjustable member and the second slot is arcuately shaped along the second adjustable member.

A method of preparing a tunnel in a femur for receipt of an anterior cruciate ligament (ACL) replacement graft using a femoral drill guide assembly is provided. The method includes grasping a handle portion of the femoral drill guide assembly. The femoral drill guide assembly can include (i) a parallel slider movable coupled relative to the handle portion along a first plane (ii) a perpendicular slider movably coupled relative to the parallel slider along a second plane, (iii) a feeder guide coupled to the perpendicular slider, and (iv) a receiving guide coupled to the handle portion.

A funnel-shaped structure extending from a receiving guide is positioned onto a native ACL footprint. The parallel slider is adjusted relative to the handle portion along the first plane. The perpendicular slider is adjusted relative to the parallel slider. The feeder guide is located at a desired location on a femoral cortex of the femur based on the adjusting of the parallel and perpendicular sliders. A pin is passed through the feeder guide. The pin is received with the funnel-shaped structure on the receiving guide. The tunnel is drilled based on the position of the pin.

According to other features, adjusting the parallel slider includes slidably negotiating a first locating member disposed on one of the parallel slider and the handle portion along a first arcuate slot formed in the other of the parallel slider and the handle portion. Adjusting the perpendicular slider includes slidably negotiating a second locating member disposed on one of the perpendicular slider and the parallel slider along a second arcuate slot formed in the other of the perpendicular slider and the parallel slider.

Further areas of applicability of the present disclosure will become apparent from the description provided hereinafter. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only and are not intended to limit the scope of the present disclosure.

DETAILED DESCRIPTION

The following description is merely exemplary in nature and is not intended to limit the present disclosure, its application, or uses. Examples are provided so that this disclosure will be thorough, and will fully convey the scope to those who are skilled in the art. Numerous specific details are set forth such as examples of specific components, devices, systems and/or methods, to provide a thorough understanding of the present disclosure. It will be apparent to those skilled in the art that specific details need not be employed, that examples shown herein may be embodied in many different forms and that neither should be construed to limit the scope of the disclosure.

The present teachings and related discussion are directed primarily to a femoral ACL drill guide assembly used to prepare a femoral tunnel for ACL fixation. It will be appreciated, however, that the femoral ACL drill guide assembly may be used in other procedures to prepare a tunnel in other bones and the following description is not intended to be limiting to preparation of a femoral tunnel for ACL reconstruction.

Figures 1, 2:
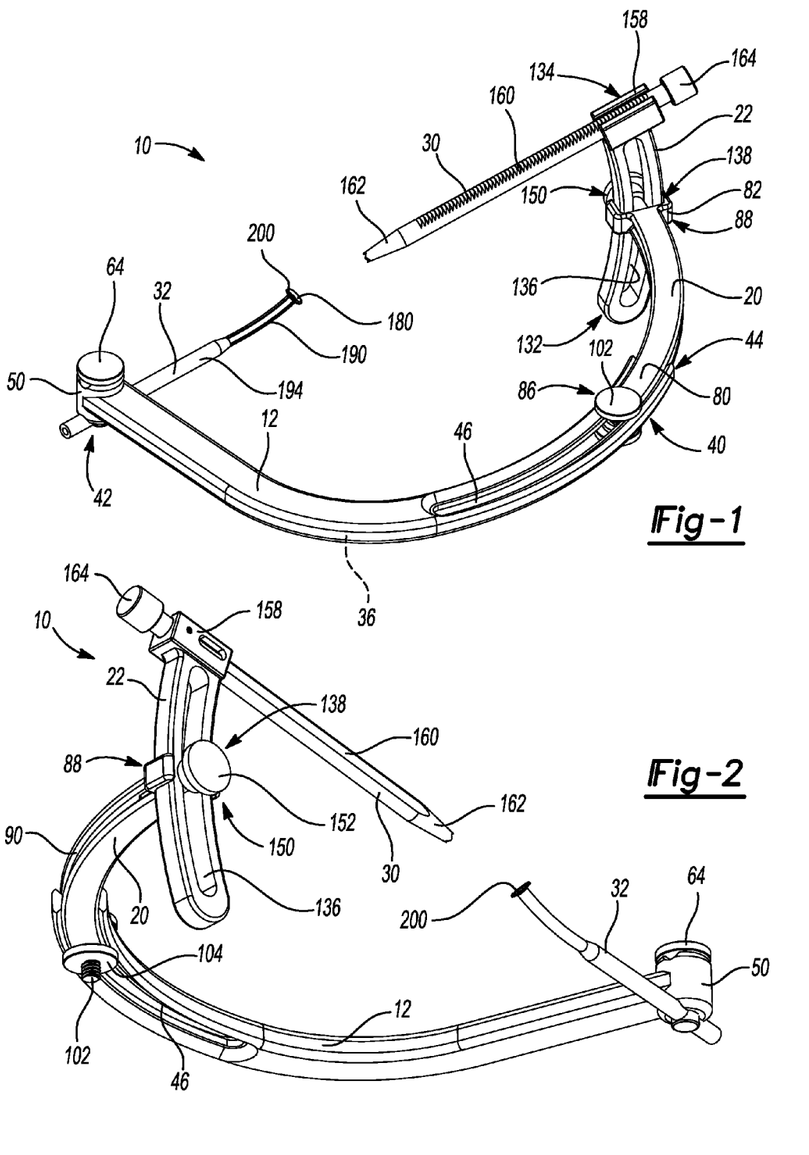
FIG. 1 is a first perspective view of a femoral ACL drill guide assembly configured for outside-in drilling and inside-out reaming and constructed in accordance to one example of the present disclosure.
FIG. 2 is a second perspective view of the femoral ACL drill guide assembly of FIG. 1.
Figure 3:
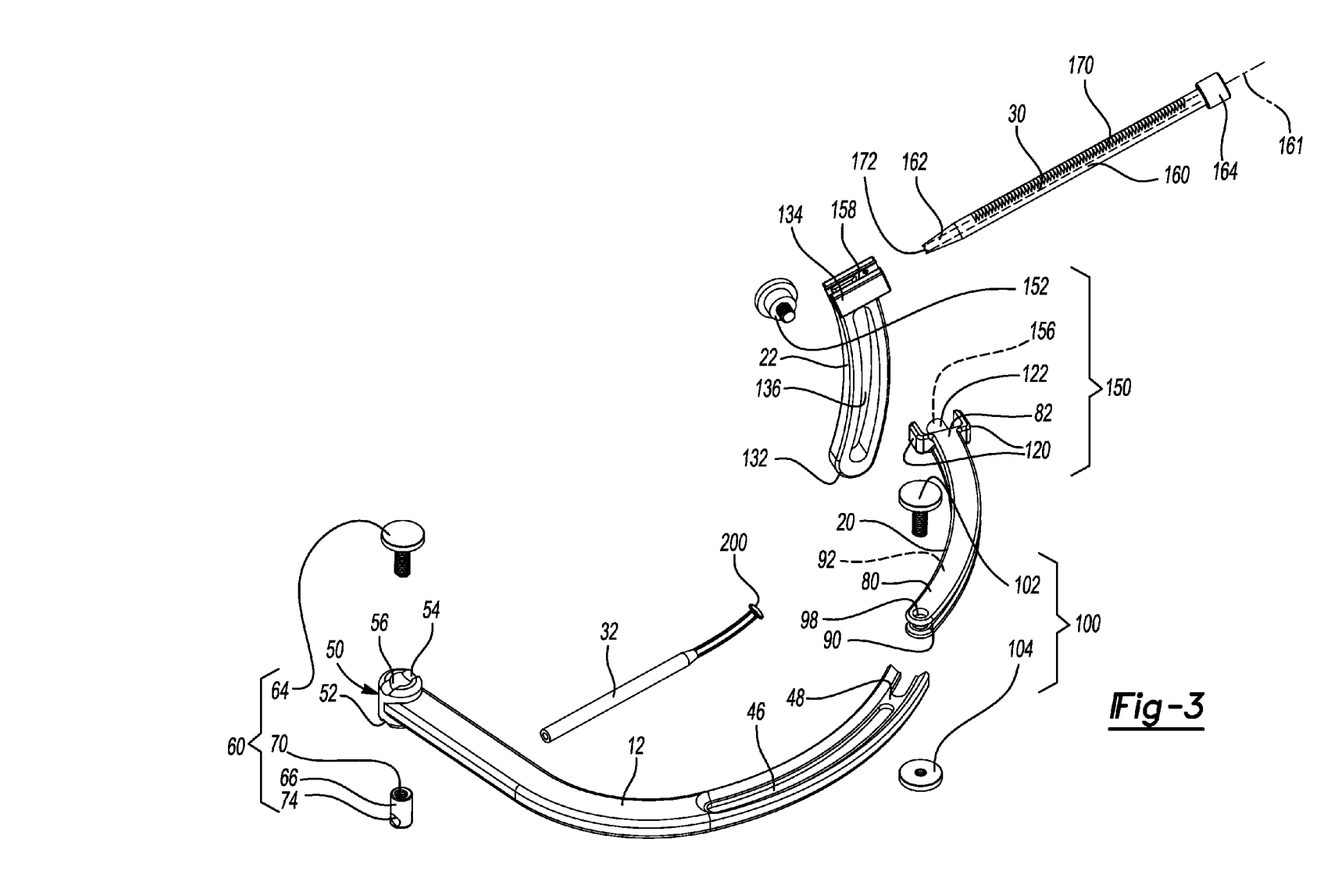
FIG. 3 is an exploded view of the femoral ACL drill guide assembly of FIG. 1.

With initial reference to FIGS. 1-3, a femoral drill guide assembly constructed in accordance to one example of the present disclosure is shown and generally identified at reference numeral 10. As will become appreciated from the following discussion, the femoral drill guide assembly 10 is particularly suited to allow for outside-in drilling (from the outside lateral cortex of the femur into the intercondylar notch) and inside-out reaming (from the intercondylar notch toward the outside lateral cortex). In particular, the femoral drill guide assembly 10 allows for adjustment in two planes. Moreover, the femoral drill guide assembly 10 provides structure to direct a guide wire inserted from the outside lateral cortex of the femur, into the intercondylar notch and out of a skin incision adjacent to the patella.

The femoral drill guide assembly 10 can generally include a handle portion 12, a parallel slider 20, a perpendicular slider 22, a feeder guide 30 and a receiving guide 32. The handle portion 12 can extend along a first plane 36 between a first handle end 40 and an opposite second handle end 42. The first handle end 40 can include a first adjustable mating portion 44 formed thereon. The handle portion 12 is generally arcuately shaped. The first adjustable mating portion 44 can be defined by a first slot 46 formed in the handle portion 12. The first slot 46 can be arcuately shaped and provided near the first handle end 40. The first slot 46 can terminate at a catch 48 at the first handle end 40. The catch 48 can act as a stop at one end of the handle portion 12 that corresponds to maximum travel of the parallel slider relative to the handle portion 12.

A locating hub 50 can be provided at the second handle end 42. The locating hub 50 can further include a first arcuate inset 52 and a second arcuate inset 54 (FIG. 3). A central passage 56 can be formed through the locating hub 50 in a direction generally perpendicular to the first plane 36. A locking assembly 60 (FIG. 3) can cooperate with the locating hub 50 for adjustably locking the receiving guide 32 to the handle portion 12. The locking assembly 60 can include a threaded screw 64 and receiving nut 66. The receiving nut 66 can include a threaded female portion 70 that threadably receives the threaded screw 64. The receiving nut 66 can be partially received by the central passage 56 of the locating hub 50.

The receiving nut 66 can further include an opening 74 that slidably receives the receiving guide 32. Rotation of the threaded screw 64 in a tightening direction causes the receiving nut 66 to be further urged into the central passage 56 resulting in the receiving guide 32 to be incrementally fixed against the locating hub 50 at the first arcuate inset 52. The receiving guide 32 can therefore be adjustably secured in a linear direction along its axis and rotatably adjusted around an axis defined by the central passage 56. In this regard, the receiving guide 32 may be positioned at a plurality of locations and orientations relative to the handle portion 12.

Figure 5:
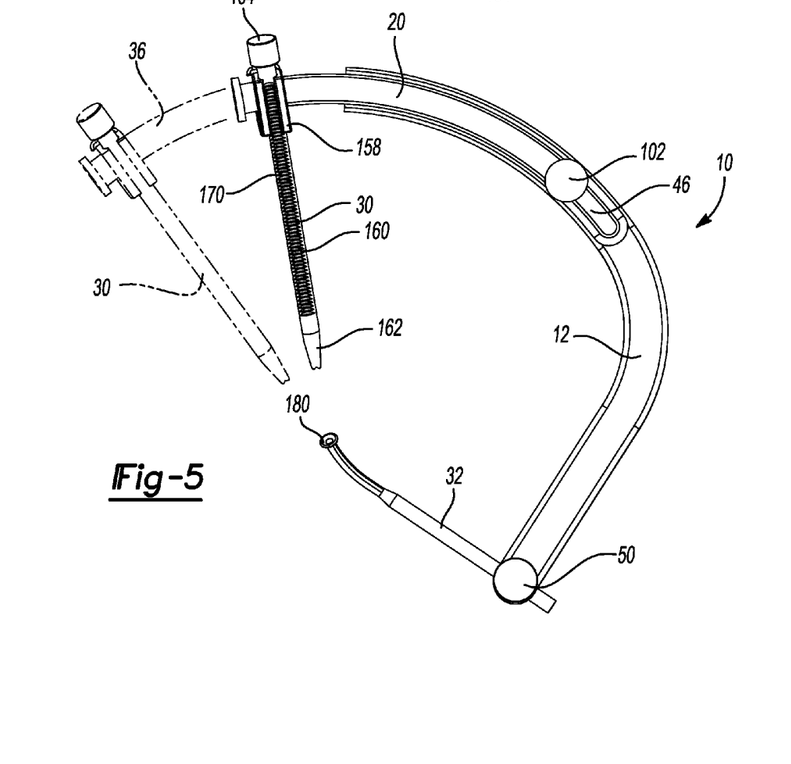
FIG. 5 is a front view of the femoral ACL drill guide assembly of FIG. 1 and shown with a parallel slider adjustable along a first plane.

With continued reference to FIGS. 1-3 and further reference to FIG. 5, the parallel slider 20 will be further described. The parallel slider 20 generally extends between a parallel slider first end 80 and an opposite parallel slider second end 82. The parallel slider 20 can have a second adjustable mating portion 86 and a third adjustable mating portion 88. The first adjustable mating portion 44 of the handle portion 12 and the second adjustable mating portion 86 of the parallel slider 20 selectively move relative to each other causing the parallel slider 20 to move relative to the handle portion 12 between a plurality of positions along the first plane 36 (FIG. 5).

The parallel slider 20 can include outer grooves 90 and 92 (FIG. 3) configured to slidably receive the handle portion 12 near the first slot 46. The handle portion 12 generally tracks along the grooves 90, 92 during adjustment of the parallel slider 20 along the first plane 36. The first end 80 of the parallel slider 20 defines a passage 98. The second adjustable mating portion 86 comprises a first locating member 100. The first locating member 100 can collectively comprise a first screw 102 that threadably mates with a receiving disk 104. The first screw 102 is received by the passage 98 and is movable between a locked position and an unlocked position. In the locked position the first locating member 100 is fixed to the handle portion 12. In the unlocked position, the first locating member 100 moves along the first slot 46 and the parallel slider 20 moves relative to the handle portion 12. The second end 82 of the parallel slider 20 includes a pair of outer arms 120 and a locating boss 122.

Figure 6:
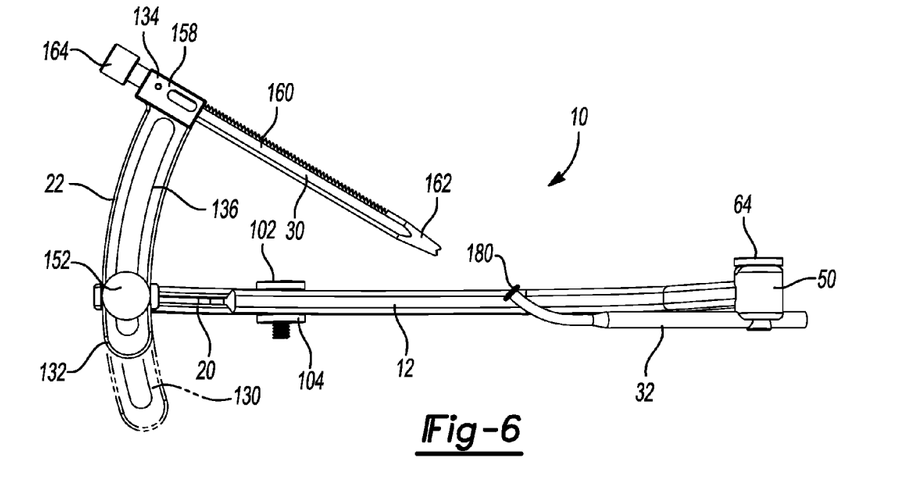
FIG. 6 is a side view of the femoral ACL drill guide assembly of FIG. 1 and shown with a perpendicular slider adjustable along a second plane.

With continued reference to FIGS. 1-3 and further reference to FIG. 6, the perpendicular slider 22 will be further described. The perpendicular slider 22 generally extends along a second plane 130 between a perpendicular slider first end 132 and an opposite perpendicular slider second end 134. A second slot 136 can be defined through the perpendicular slider 22. The perpendicular slider 22 can have a fourth adjustable mating portion 138 thereon. In the example shown, the fourth adjustable mating portion 138 is the second slot 136. The third adjustable mating portion 88 of the parallel slider 20 and the fourth adjustable mating portion 138 of the perpendicular slider 122 selectively move relative to each other causing the perpendicular slider 22 to move relative to the parallel slider 20 between a plurality of positions along the second plane 130 (FIG. 6). In the example provided, the first plane 36 is perpendicular to the second plane 130 allowing adjustment along two transverse planes. It will be appreciated, however, that the femoral drill guide assembly 10 may be configured such that the first plane 36 and second plane 130 are not transverse while still allowing adjustment along two distinct planes.

The third adjustable mating portion 88 comprises a second locating member 150 (FIG. 3). The second locating member 150 can collectively comprise a second screw 152 that threadably mates with a receiving member 156 defined in the boss 122. The second screw 152 extends through the second slot 136 and selectively mates with the receiving member 156 between a locked position and an unlocked position. In the locked position, the perpendicular slider 22 is fixed to the parallel slider 20. In the unlocked position, the second locating member 150 moves along the second slot 136 and the perpendicular slider 22 moves relative to the parallel slider 20. The boss 122 is guided along the second slot 136 while the outer arms 120 of the parallel slider 20 bound the perpendicular slider 22. The slider second end 134 includes a receiving channel 158 configured to locate the feeder guide 30.

The feeder guide 30 will now be described in greater detail. The feeder guide 30 generally includes a longitudinal feeder guide body 160 that extends along a feeder guide body axis 161 (FIG. 3) between a distal locating end 162 and a proximal adjusting end 164. The longitudinal feeder guide body 160 includes ribs 170 thereon. The feeder guide 30 is adjustable secured at the receiving channel 158 and translatable within the receiving channel 158 along the feeder guide body axis 161. The feeder guide 30 defines a cannulation 172 through the feeder guide body 160.

Figure 4:
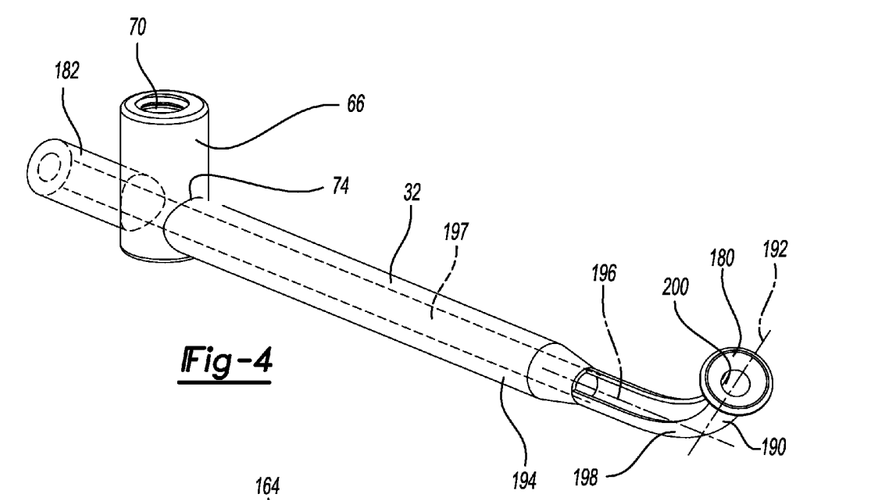
FIG. 4 is a perspective view of a receiving guide of the femoral ACL drill guide assembly of FIG. 1.

With general reference to FIGS. 1-3 and particular reference to FIG. 4, the receiving guide 32 will be described in greater detail. The receiving guide 32 includes a receiving end 180 and an opposite end 182. The receiving guide 32 has a first guide body portion 190 that extends along a first axis 192 and a second guide body portion 194 that extends along a second axis 196. The second guide body portion 194 defines a cannulation 197. The first and second guide body portions 190 and 194 converge at an intermediate non-linear body portion 198. The first axis 192 and the second axis 196 intersect. The receiving guide 32 can be adjustably secured to the second handle end 42 at the locating hub 50. The receiving guide 32 can therefore be adjustably secured in a linear direction along and around the axis 196. In this regard, the receiving guide 32 may be positioned at a plurality of locations and orientations relative to the handle portion 12.

The receiving end 180 includes a generally conical structure 200 and is generally funnel shaped. As will become appreciated herein, the funnel-shaped nature of the receiving end 180 allows a guide wire passed from the feeder guide 30 to be successfully received by the conical structure 200 from a number of different orientations. A guide wire received by the conical structure 200 can be slidably directed along an inner surface of the intermediate portion 198 and into the cannulation 197 of the second guide body portion 194. Because the conical structure 200 acts as a funnel, the aim of the guide wire need not be with elevated precision. Rather, the conical structure 200 can slidably guide the guide wire from an area defined generally by the perimeter of the conical structure 200 and into the receiving guide 32. The conical structure 200 of the receiving end 180 acts as an aid for arthroscopic visualization of the graft footprint prior to drilling. Moreover, the radial range of motion of the feeder guide 30 allows it to remain in-line with the conical structure 200 of the receiving end 180 of the receiving guide 32 while also allowing a surgeon to urge the feeder guide 30 up against the outer surface of the femur (see also FIG. 7) during drilling.

Figure 7:
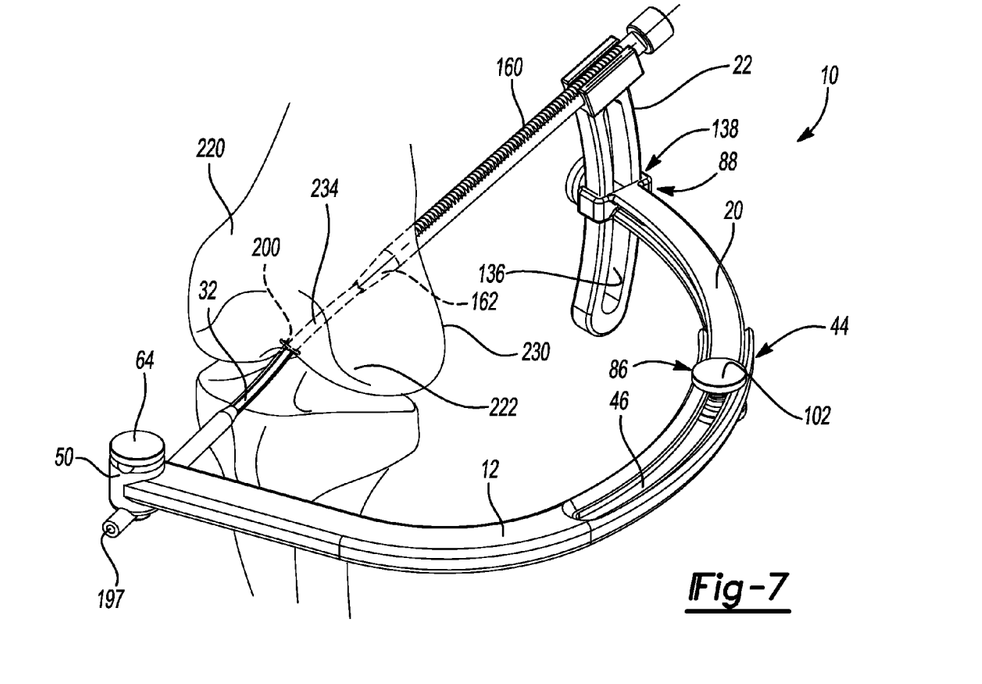
FIG. 7 is a lateral view of a left knee showing the femoral ACL drill guide assembly positioned for outside-in drilling.

An exemplary method of using the femoral drill guide assembly 10 will now be described with reference to FIG. 7. Because the femoral drill guide assembly 10 provides adjustment in two planes (plane 36, FIG. 5 and plane 130, FIG. 6), the range of motion of the femoral drill guide assembly 10 allows for almost unlimited drill placement options on femur 220 without sacrificing footing on femoral condyle 222. This large range of motion mitigates the guide's physical limitations as a factor in drill placement. In this regard, the versatility of the femoral drill guide assembly 10 allows the surgeon to choose drill placement on the sole basis of creating the hole in the anatomic location that provides the highest quality bone. Prior art single plane "outside-in" reamers can create complicated coordinate systems because they often must be rotated out of plane with respect to the joint line to reach the desired drilling location. Even when rotated out of plane, such prior art single plane instruments still have a limited range of motion that limits socket placement options. Similarly, a prior art inter-articular (inside-out) approach to guide wire placement is often inaccurate. The femoral drill guide assembly 10 provides greater adjustability to improve upon these prior art limitations.

In other benefits, the femoral drill guide assembly 10 provides a simpler coordinate system over prior art drill guide configurations. Explained further, current single-planar drill guide options force the surgeon to rotate the drill guide out-of-plane to get higher up (superior) on the femur 220, giving the surgeon a complicated coordinate system with which to locate the correct drilling location. The dual-planar, on-point range of motion allows the surgeon to hold the handle portion 12 parallel to the joint line and easily locate the correct drill location by using the angular set of coordinates on each one of the sliding portions of the femoral drill guide assembly 10. In this way, a simple perpendicular-axis coordinate system is provided by the femoral drill guide assembly 10. Further, as identified above, the conical structure 200 of the receiving end 180 of the receiving guide 32 allows for arthroscopic visualization of the graft footprint before drilling.

In one exemplary method of using the femoral guide assembly 10, the surgeon first assesses and prepares the distal femur 220. In this regard, the native ACL footprint can initially be determined after excising the damaged ACL. The conical structure 200 of the receiving guide 32 can be placed on the native ACL footprint. In some patients it may be desired to further assess the posterior cruciate ligament (PCL). If there is not sufficient space to accommodate a new ACL, it may be necessary to remove some of the bone within the intercondylar notch to allow for enough space for the new ACL to be placed without impingement.

Once the conical structure 200 of the receiving guide 32 is located, the parallel slider 20 may be adjusted relative to the handle portion 12 along the plane 36 (again see FIG. 5). Additionally, the perpendicular slider 22 may be adjusted relative to the parallel slider 20 along the plane 130 (again see FIG. 6). Of note, the movement of the perpendicular slider 22 allows the surgeon to locate more superiorly on the femoral cortex 230 to reach thicker, more desirable cortical bone. The adjustments on both planes 36 and 130 are made until the surgeon finds a desirable location on the lateral cortex 230 where the distal end 162 of the feeder guide 30 is placed.

The feeder guide 30 is then ratcheted tightly against the lateral cortex 230 and a guide pin 234 is drilled in through the lateral cortex 230 ("outside-in" as referred to herein). The guide pin 234 is received by the conical structure 200 of the receiving guide 32. In some examples, the guide pin 234 can be passed through the cannulation 197 of the receiving guide 32 and come out of a medial skin incision adjacent the patella. The guide pin 234 is formed of flexible material such as Nitinol.

Figure 8:
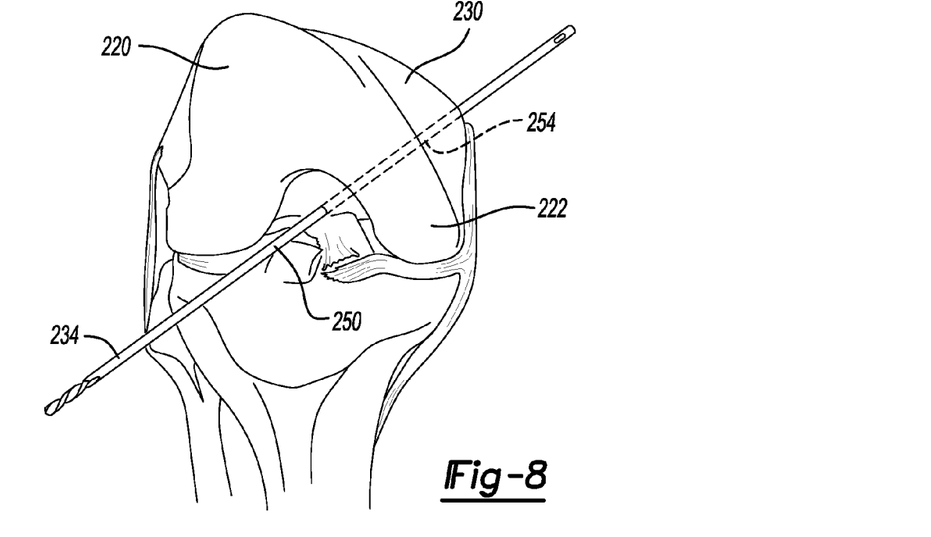
FIG. 8 is an anterior view of the left knee of FIG. 7 showing an exemplary femoral aimer drilling a femoral tunnel along an inside-out path through the lateral femoral cortex.
Figure 9:
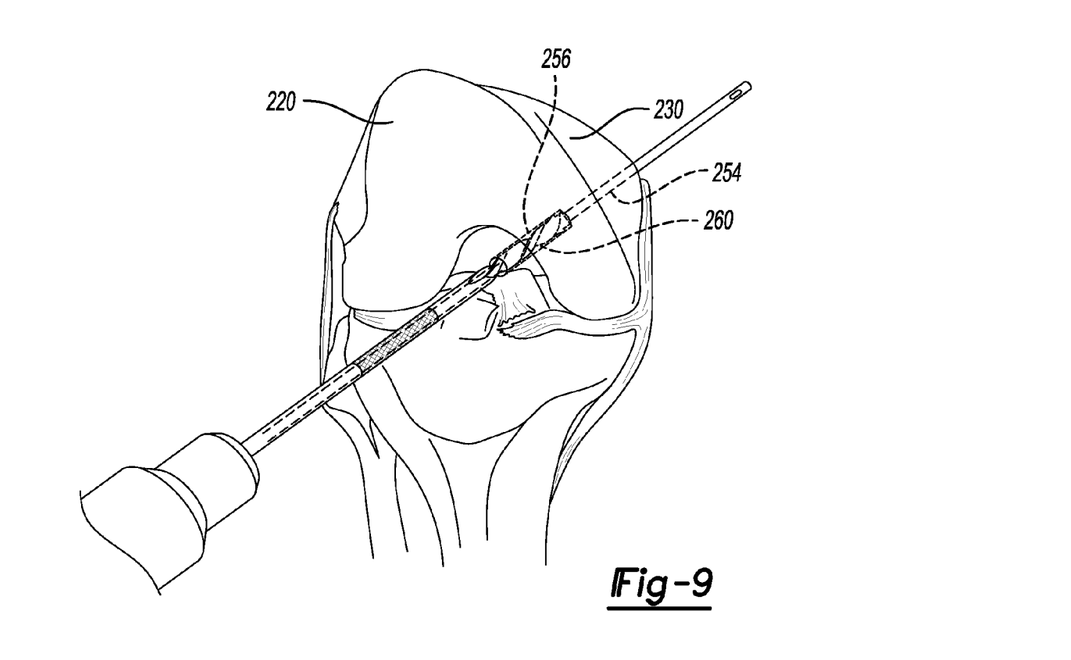
FIG. 9 is an anterior view of the left knee of FIG. 8 showing a reamer preparing a counterbore along the prepared femoral tunnel.

Referencing now FIGS. 8 and 9, the femoral drill guide assembly 10 can then be removed. A reamer 250 can then be used to drill over the guide pin 234 extending along the prepared femoral tunnel from inside the joint space and out through the lateral cortex 230 ("inside-out" as referred to herein) The reamer 250 can be located through a medial incision adjacent the patella (not specifically shown). In one example, a 4.5 mm reamer can be used. Once an initially reamed femoral tunnel 254 has been prepared, the reamer 250 is removed and a larger diameter second reamer 260 is used to prepare a counterbore 256. Depending on the size of graft used, the reamer 260 can be between 6 mm to 12 mm in diameter. Other sizes are contemplated. In one example the second reamer 260 is drilled to a 25 mm depth. The second reamer 260 can have a flexible section represented by crosshatching in FIG. 9. Other configurations are contemplated.

Figure 10:
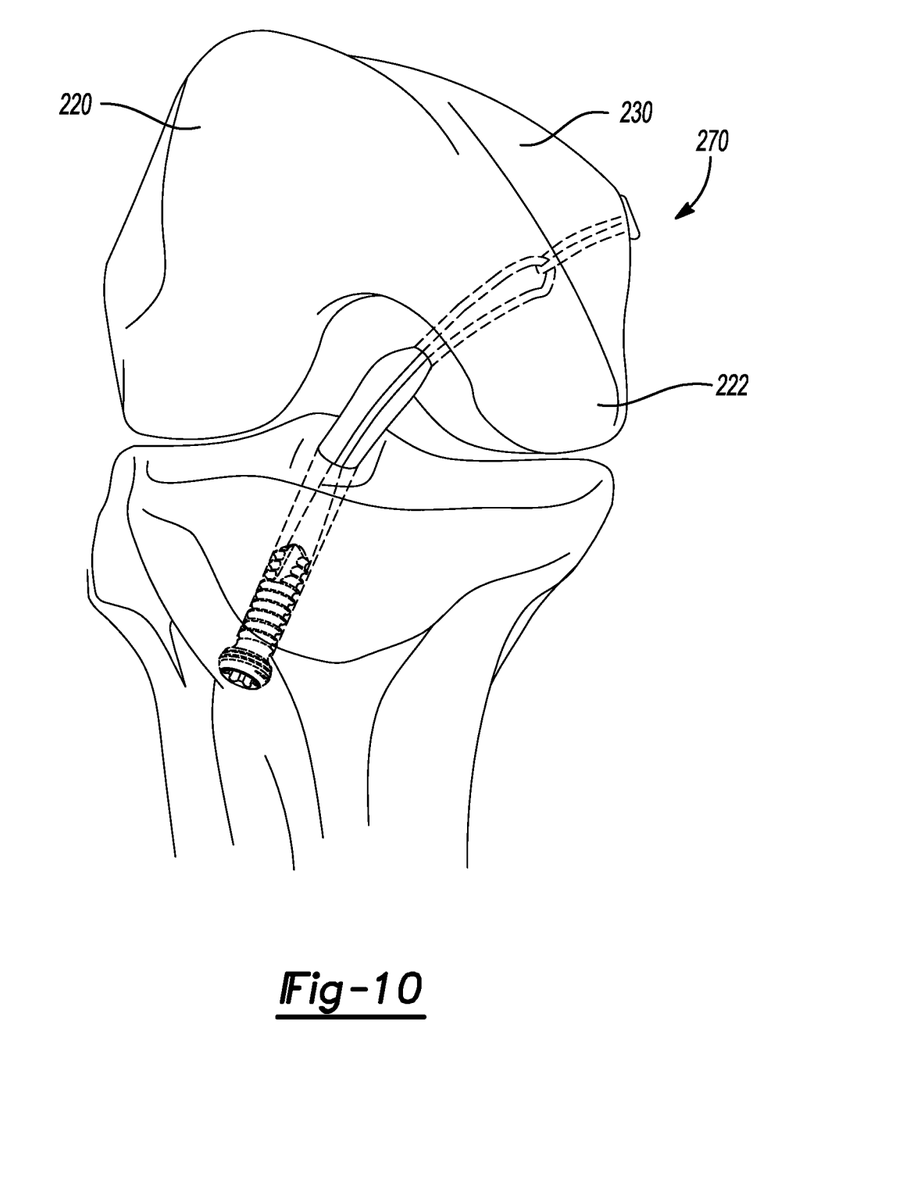
FIG. 10 is an anterior view of the left knee of FIG. 9 showing an exemplary ToggleLoc™ femoral fixation device using a ZipLoop™ for ACL reconstruction.

Turning now to FIG. 10, an exemplary suspensory fixation implant 270 can be implanted into the prepared tunnel. In the example shown, the suspensory fixation implant 270 is a ToggleLoc™ femoral fixation device having a ZipLoop™. Additional description of the suspensory fixation implant 270 and other suitable implants may be found in commonly owned U.S. Pat. No. 8,740,939, the contents of which are expressly incorporated herein by reference.

While one or more specific examples or aspects have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

The terminology used herein is for the purpose of describing particular example implementations only and is not intended to be limiting. As used herein, the singular forms "a," "an," and "the" may be intended to include the plural forms as well, unless the context clearly indicates otherwise. The term "and/or" includes any and all combinations of one or more of the associated listed items. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

What is claimed is:

1. A femoral drill guide assembly comprising:
   a handle portion that extends along a first plane between a first handle end and an opposite second handle end, the first handle end including a first adjustable mating portion formed thereon;
   a parallel slider that extends between a parallel slider first end and an opposite parallel slider second end, the parallel slider having a second and a third adjustable mating portion thereon, wherein the first and second adjustable mating portions selectively move relative to each other causing the parallel slider to move relative to the handle portion between a plurality of positions along the first plane;
   a perpendicular slider that extends along a second plane between a perpendicular slider first end and an opposite perpendicular slider second end, the perpendicular slider having a fourth adjustable mating portion thereon, wherein the parallel and perpendicular sliders are coupled by way of the third and fourth adjustable mating portions, and the third and fourth adjustable mating portions are configured to selectively move relative to each other along the second plane but not the first plane, thereby causing the perpendicular slider to move relative to the parallel slider between a plurality of positions along the second plane but not the first plane;
   a feeder guide movably coupled to the perpendicular slider, the feeder guide including a cannulation configured to direct a guide wire along a first longitudinal axis; and
   a receiving guide coupled to the handle portion, the receiving guide having a receiving end including an aperture configured to accept the guide wire from the feeder guide, wherein the first longitudinal axis intersects with the aperture.

2. The femoral drill guide assembly of claim 1 wherein the receiving end of the receiving guide includes a funnel-shaped surface formed about the aperture, the funnel-shaped surface configured to guide the guidewire through the aperture.

3. The femoral drill guide assembly of claim 2 wherein the receiving guide comprises a first guide body portion that extends along a first axis and a second guide body portion that extends along a second axis, wherein the first and second guide body portions converge at an intermediate non-linear body portion, wherein the first and second axes intersect.

4. The femoral drill guide assembly of claim 3 wherein the receiving guide is cannulated.

5. The femoral drill guide assembly of claim 3 wherein the receiving guide is rotatably fixed to the second handle end, whereby the receiving guide is configured to selectively rotate along the second axis.

6. The femoral drill guide assembly of claim 3 wherein the second guide body portion of the receiving guide is configured to adjustably translate along the second axis relative to the handle portion to locate the receiving end, including the aperture, at a plurality of positions.

7. The femoral drill guide assembly of claim 1 wherein one of the first and second adjustable mating portions comprises a first slot and the other of the first and second adjustable mating portions comprises a first locating member, wherein the first locating member is configured to slidably negotiates along the first slot causing the parallel slider to move relative to the handle portion between the plurality of positions along the first plane.

8. The femoral drill guide assembly of claim 7 wherein the first locating member collectively comprises a first screw that threadably mates with a receiving disk, the first screw movable between (i) a locked position with the disk wherein the first locating member is fixed to the handle portion and (ii) an unlocked position with the disk wherein the first locating member moves along the first slot and the parallel slider moves relative to the handle portion.

9. The femoral drill guide assembly of claim 8 wherein the first slot is arcuately shaped along the handle portion.

10. The femoral drill guide assembly of claim 1 wherein one of the third and fourth adjustable mating portions comprises a second slot and the other of the third and fourth adjustable mating portions comprises a second locating member, wherein the second locating member is configured to slidably negotiates along the second slot causing the perpendicular slider to move relative to the parallel slider between the plurality of positions along the second plane but not the first plane.

11. The femoral drill guide assembly of claim 10 wherein the second locating member collectively comprises a second screw that threadably mates with a receiving member, the second screw movable between (i) a locked position with the receiving member wherein the second locating member is fixed to the perpendicular slider and (ii) an unlocked position with the receiving member wherein the second locating member moves along the second slot and the perpendicular slider moves relative to the parallel slider.

12. The femoral drill guide assembly of claim 11 wherein the second slot is arcuately shaped along the perpendicular slider.

13. The femoral drill guide assembly of claim 1 wherein the parallel slider is arcuately shaped.

14. The femoral drill guide assembly of claim 1 wherein the perpendicular slider is arcuately shaped.

15. A femoral drill guide assembly comprising:
   a handle portion that extends along a first plane and including a first adjustable mating portion formed thereon;
   a first adjustable member having a second and a third adjustable mating portion formed thereon, wherein the first and second adjustable mating portions are configured to selectively move relative to each other causing the first adjustable member to move relative to the handle portion between a plurality of positions along the first plane;
   a second adjustable member that extends along a second plane, the second adjustable member having a fourth adjustable mating portion thereon, wherein the first and second adjustable members are coupled by way of the third and fourth adjustable mating portions, and the third and fourth adjustable mating portions are configured to selectively move relative to each other causing the second adjustable member to move relative to the first adjustable member between a plurality of positions along the second plane but not the first plane, the first and second planes being distinct;
   a feeder guide movably coupled to the second adjustable member, the feeder guide including a cannulation configured to direct a guide wire along a first longitudinal axis; and
   a receiving guide coupled to the handle portion, the receiving guide having a funnel-shaped receiving end including an aperture configured to accept the guide wire from the feeder guide, wherein the first longitudinal axis intersects with the aperture.

16. The femoral drill guide assembly of claim 15 wherein the receiving guide comprises a first guide body portion that extends along a first axis and a second guide body portion that extends along a second axis, wherein the first and second guide body portions converge at an intermediate non-linear body portion, wherein the first and second axes intersect.

17. The femoral drill guide assembly of claim 15 wherein one of the first and second adjustable mating portions comprises a first slot and the other of the first and second adjustable mating portions comprises a first locating member, wherein the first locating member is configured to slidably negotiates along the first slot causing the first adjustable member to move relative to the handle portion between the plurality of positions along the first plane.

18. The femoral drill guide assembly of claim 17 wherein the first locating member collectively comprises a first screw that threadably mates with a receiving disk, the first screw movable between (i) a locked position with the disk wherein the first locating member is fixed to the handle portion and (ii) an unlocked position with the disk wherein the first locating member is configured to move along the first slot and the first adjustable mating portion is configured to move relative to the handle portion.

19. The femoral drill guide assembly of claim 15 wherein one of the third and fourth adjustable mating portions comprises a second slot and the other of the third and fourth adjustable mating portions comprises a second locating member, wherein the second locating member is configured to slidably negotiates along the second slot causing the second adjustable member to move relative to the first adjustable member between the plurality of positions along the second plane but not the first plane.

20. The femoral drill guide assembly of claim 19 wherein the second locating member collectively comprises a second screw that threadably mates with a receiving member, the second screw movable between (i) a locked position with the receiving member wherein the second locating member is fixed to the second adjustable member and (ii) an unlocked position with the receiving member wherein the second locating member is configured to moves along the second slot and the second adjustable member is configured to move relative to the first adjustable member.

21. The femoral drill guide assembly of claim 20 wherein the first slot is arcuately shaped along the first adjustable member and the second slot is arcuately shaped along the second adjustable member.

22. The femoral drill guide assembly of claim 15, wherein the funnel-shaped receiving end of the receiving guide includes a funnel-shaped surface formed about the aperture, the funnel-shaped surface configured to guide the guidewire through the aperture.

\* \* \* \* \*

UNITED STATES PATENT AND TRADEMARK OFFICE
CERTIFICATE OF CORRECTION

PATENT NO.         : 9,955,982 B2
APPLICATION NO.    : 14/691026
DATED              : May 1, 2018
INVENTOR(S)        : Meridew et al.

Page 1 of 1

It is certified that error appears in the above-identified patent and that said Letters Patent is hereby corrected as shown below:

In the Claims

In Column 10, Line 34, in Claim 7, delete "negotiates" and insert --negotiate-- therefor In Column 12, Line 32, in Claim 20, delete "moves" and insert --move-- therefor Signed and Sealed this
Second Day of April, 2019

Andrei Iancu
*Director of the United States Patent and Trademark Office*